United States Patent
Massey et al.

[11] Patent Number: 5,857,969
[45] Date of Patent: Jan. 12, 1999

[54] PNEUMATIC PRESSURE PROBE

[75] Inventors: Anthony D. Massey; Christopher Crowhurst, both of Chippenham; Malcolm Redman, Frocester, all of Great Britain

[73] Assignee: O.B.F. Labs Limited, Great Britain

[21] Appl. No.: 836,967
[22] PCT Filed: Nov. 14, 1995
[86] PCT No.: PCT/GB95/02674
§ 371 Date: Jul. 28, 1997
§ 102(e) Date: Jul. 28, 1997
[87] PCT Pub. No.: WO96/16589
PCT Pub. Date: Jun. 6, 1996

[30] Foreign Application Priority Data

Nov. 26, 1994 [GB] United Kingdom ............... 9423899

[51] Int. Cl.[6] ................. A61B 3/16; A61B 5/022
[52] U.S. Cl. ........................................... 600/398
[58] Field of Search ........................... 600/398–406; 73/49.4, 52, 78, 81–85

[56] References Cited

U.S. PATENT DOCUMENTS

| | | |
|---|---|---|
| 3,272,001 | 9/1966 | Adise . |
| 3,628,526 | 12/1971 | Bigliano . |
| 4,213,464 | 7/1980 | Katz et al. . |
| 4,883,056 | 11/1989 | Langham . |
| 4,886,066 | 12/1989 | Ingalz et al. . |
| 5,190,042 | 3/1993 | Hock ........................................... 600/45 |
| 5,546,941 | 8/1996 | Zeimer et al. ........................... 600/405 |

FOREIGN PATENT DOCUMENTS

| | | |
|---|---|---|
| 0067910 | 12/1982 | European Pat. Off. . |
| 0315329 | 5/1989 | European Pat. Off. . |
| 9001891 | 3/1990 | WIPO . |

OTHER PUBLICATIONS

"Measuring Eyeball Pressure with a Crystal Oscillator" *Electronics*, vol. 34, No. 36, pp. 64 and 65 (Sep. 8, 1961).

*Primary Examiner*—John P. Lacyk
*Assistant Examiner*—Samuel Gilbert
*Attorney, Agent, or Firm*—Peter J. Manus, Esq.

[57] ABSTRACT

A pneumatic pressure probe for use in measuring pulsatile ocular blood flow comprises a housing consisting of an air tight bearing defining a pressure chamber, a piston having an axial bore communicating with the pressure chamber, the proximal end of the piston carrying a counter balancing weight and being received in the pressure chamber and the distal end of the piston extending outwardly of the housing and carrying a disposable sensing head. A transparent membrane is integrally attached to the sensing head and is substantially perpendicular to the piston axial bore and an interior channel through which light is emitted to the membrane from an LED mounted in the housing. The probe allows the patients visual axis to be aligned with the axial bore of the piston by focusing on the light source during measurement enabling the applanated comae and sensing membrane to be maintained substantially parallel and substantially perpendicular with the axial bore of the piston.

14 Claims, 1 Drawing Sheet

PNEUMATIC PRESSURE PROBE

BACKGROUND OF THE INVENTION

This invention relates to pneumatic pressure probes for use, in particular, though not exclusively, in measuring change in intra-ocular pressure and in measuring pulsatile ocular blood flow.

More specifically this invention is concerned with pneumatic pressure probes, also known as pneumotonometers. These are similar to applanation tonometers which operate on the principle of applanation, or flattening, of the cornea in order to monitor pressure changes in the eye. (In fact pneumotonometers tend to indent the cornea as well as flatten it, but the magnitude of this indentation is microscopic). As the pressure in the eye changes the pressure required to applanate the cornea changes proportionately. When used in combination with a pressure sensing device, which may, for example, be incorporated in a computerised tonograph, analogue electronic signals representing continuous intra-ocular pressure changes may be produced and processed in order to calculate a value representing the pulsatile blood flow through the eye.

It has been demonstrated that ocular blood flow is of significant importance in research into, and also potentially for diagnosing and monitoring treatment of, many ocular conditions including glaucoma, diabetic retinopathy, macular degeneration and arteriosclerosis,as well as vascular abnormalities such as carotid stenosis.

European Patent number EP 0315329 describes an applanation-type pneumatic pressure probe for use in measuring fluid pressure within an organ such as an eye. This probe comprises a hollow handle defining a pressure chamber, a hollow shaft which is slidably received within the handle, and a sensor head including a contact face, mounted on a distal end of the shaft. A proximal end of the shaft is received in the pressure chamber but is not influenced by the pressure within the chamber. However, this probe design has many inherent performance problems associated with, in particular, undesirably high friction levels between the hollow handle and the piston. The piston is relatively long in comparison to the sensor head, which is itself relatively large and heavy in relation to the piston, especially where the piston and sensor head are made largely of metal. Furthermore, many problems are associated with the relatively high weights of the component parts of the probe and the relative dimensions of these parts.

Further problems with this known probe design arise from the fact that the piston is prone to damage, especially by bending, due to its relatively long length. A bent probe will not move freely in relation to the shaft, resulting in very poor measurements.

In order to obtain sufficiently accurate measurements, the contact face of the sensor head should be aligned substantially parallel to the applanated cornea, substantially perpendicular to the visual axis of the patient. However, with no means to ensure that the patient is correctly aligned with the probe and sensor head, variable results are often obtained due to poor alignment.

Furthermore, this known probe must be used in combination with a removable membrane mounted on the sensor head, in order to avoid direct contact between the patient's eye and the contact face of the sensor head (for hygiene reasons). Every time the membrane must be removed for cleaning, subsequent replacement of the membrane often results in incorrect seating of the membrane on the sensor head. Since the seating of the membrane is critical to the measurements obtained from the probe, with no means for guaranteeing that the seating of the membrane is constant, the repeatability of probe measurements cannot be ensured.

SUMMARY OF THE INVENTION

All these problems have made pressure measurements obtained from this prior art probe extremely inconsistent and inaccurate, with a very low repeatability. It is an aim of the present invention to provide an improved pneumatic pressure probe.

According to the present invention a pneumatic pressure probe comprises: a housing defining therewithin a pressure chamber; a piston having an axial bore which is in communication with the pressure chamber, a proximal end of the piston being received in the pressure chamber and a distal end of the piston extending out from the housing; a sensing head associated with the distal end of the piston and comprising a transparent sensing membrane and an interior channel which is in communication with the axial bore of the piston; and light emitting means mounted in the housing, the light emitting means in use emitting light which is visible through the transparent sensing membrane.

The sensing head is preferably mounted on the distal end of the piston. Alternatively the sensing head may be integral with the distal end of the piston.

The sensing membrane is preferably substantially perpendicular to the axial bore of the piston, the light emitting means and the axial bore of the piston preferably being located on a common axis.

One advantage of the pressure probe according to the invention is that a patient may align his or her visual axis with the axial bore of the piston by focusing on the source of the light (i.e. the light emitting means). The patient is thus provided with a visual fixation point while a measurement is being carried out, enabling the applanated cornea to be maintained in substantially perpendicular alignment with the axial bore of the piston which, in turn, maintains the sensing membrane substantially parallel to the applanated cornea in order to obtain an accurate reading.

The axial bore of the piston of the pneumatic pressure probe according to the invention is preferably of a diameter sufficiently small to enable a substantially constant pressure differential to be maintained between the pressure chamber and the sensing head. The cross-sectional area of an outer surface of the proximal end of the piston is preferably sufficiently large to cause the piston to be resiliently biased towards a fully extended position under the action of force exerted on the piston by the pressure differential across the length of the piston.

In use, the membrane is applied to the cornea and a force is exerted on the housing by the operator such that the piston is preferably maintained in a partially extended position.

An advantage of these features of the piston's dimensions is that the piston is automatically fully extended at the start of any test, prior to applanation of the eye, and the sensor head is automatically re-applied to the eye in the event of any movements of the eye away from the sensor head.

The diameter of the axial bore of the piston and the cross-sectional area of the proximal end of the piston are preferably both sufficiently small that undesirably large pressures are not exerted on the eye in use. In particular, the cross-sectional area of the proximal end of the piston is preferably sufficiently small to avoid forces acting on the outer surface of the proximal end of the piston (due to the pressure in the chamber) which would be large enough to cause an artificial increase in intra-ocular pressure.

The pneumatic pressure probe may further comprise weighting means for counterbalancing the weight of the sensing head. Preferably, the weighting means is located on the proximal end of the piston, within the pressure chamber of the housing. The weighting means may be integrally formed with the proximal end of the piston. The weighting means preferably further operates as a stopping means for preventing the piston disengaging from the housing when the piston is fully extended. The cross sectional area of the weighting means is preferably greater than or substantially equal to the cross sectional area of the proximal end of the piston.

Preferably, the housing of the probe comprises a substantially air-tight bearing in which a portion of the piston is slidably received. The bearing may be manufactured of a material having relatively low frictional effect on movement of the piston in the bearing. The bearing may be a plastics material, for example, a polyamide-imide and graphite composite. The piston may be of a relatively light alloy, for example, an aluminium alloy.

Such piston and bearing materials have been found to exhibit sufficiently low frictional effects, when the piston and bearing operate in combination, to enable the piston to move substantially freely in response to movements of an eye being monitored.

Furthermore, the piston may be relatively short in length, being preferably between substantially 25 and 30 millimeters long. The short length, in combination with the light alloy material of the piston, acts to reduce the inertia of the piston relative to known prior art pistons of relatively long length manufactured from relatively heavy materials. The sensing head is preferably also made of a relatively light material, for example, a polymer, in order to further reduce the inertia of the combined piston and sensing head.

The materials of the bearing and probe preferably each also exhibit a sufficiently high temperature tolerance to avoid substantial inaccuracies in measurements obtained with the probe due to temperature variation in the probe surroundings.

The sensing head may be a disposable head. The sensing membrane is preferably integrally attached to the disposable head. The disposable head may be pre-sterilised by gamma radiation prior to mounting of the head on the piston. This prevents potential re-alignment errors being introduced in the probe by eliminating the need for removal and subsequent replacement of the membrane in order to clean the membrane after each patient has been tested. Instead a new sensing head may be used for each patient or each eye of a patient being tested.

The housing of the probe may comprise a main body, and a front member. The front member preferably includes the air-tight bearing and may be replaceable. In this manner the front member or the piston may be replaced if either of these parts becomes damaged. This removes the need for total probe replacement when a probe is found to be performing inaccurately, for example.

The probe according to the present invention is thus capable of producing substantially consistent results. In particular the probe measurements obtained with the probe being inclined either substantially horizontally or substantially vertically are substantially the same. Additionally the chosen probe dimensions and materials result in relatively low forces being exerted upon an eye being monitored; the relatively low frictional effects, improved piston design and chosen probe materials function in combination to enable sufficiently low forces to be exerted on the eye to prevent substantial increases being induced in the intra-ocular pressure which could cause disturbance of the physiology of the eye.

The relatively high repeatability and accuracy of continuous ocular pressure changes measured with the probe according to the present invention enable accurate calculations of the pulsatile ocular blood flow to be performed by a computerised tonograph, for example.

One embodiment of the invention will now be described, by way of example only, with reference to the accompanying drawing, in which:

DETAILED DESCRIPTION OF THE PREFERRED EMBODIMENTS

Figure 1:
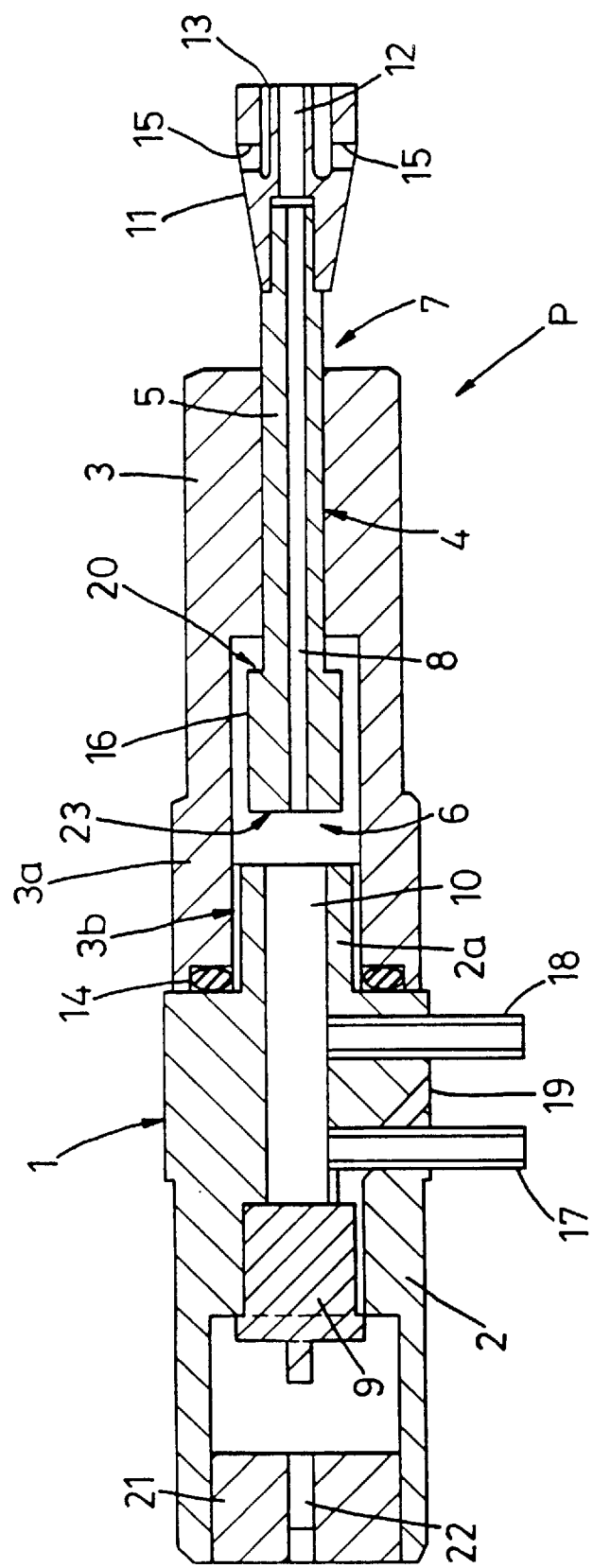
FIG. 1 is a diagrammatic cross-sectional representation of a pneumatic pressure probe according to the invention.

The pneumatic pressure probe P, of FIG. 1, is for use in a tonograph for measuring change in intra-ocular pressure.

The probe comprises a housing 1 having a rear main body 2 and a front bearing adaptor 3. The rear end 3a of the front bearing adaptor has a screw fitting 3b for engagement with a complementary fitting on a front portion 2a of the rear main body 2. An 'O' ring seal 14 is located between the main body 2 and the bearing adaptor 3 in order to form an air-tight seal between these two parts. The front bearing adaptor 3 comprises a bearing 4 located towards the front end of the bearing adaptor. A piston 5 is slidably received in substantially air-tight relationship in the bearing 4 for axial movement therein parallel to the central axis of the housing 1. The rear end 6 of the piston is received within the housing 1 and the front end 7 extends beyond the front bearing adaptor outside the housing 1.

The front bearing adaptor 3 can be unscrewed from the main body 1 so that it or the piston may be replaced should either of them become damaged or defective in any way. A low voltage light emitting diode (LED) 9 is located within the housing 1 and is mounted in the rear of the main body 2 The LED 9, the main body 2, the front bearing adaptor 3 together define a pressure chamber 10 within the probe P. The piston 5 has a restricting axial bore 8 extending along its length and in communication with the pressure chamber 10. The LED 9 is mounted in the main body 2 such that light emitted from the LED is directed through the pressure chamber and down the axial bore 8 of the piston towards the front end 7 of the piston.

A disposable tip 11 is mounted on the front end 7 of the piston and comprises a thrust nozzle 12, an integral, substantially planar, transparent membrane 13 forming a contact face of the disposable tip, and two exhaust ports 15, separate from the thrust nozzle 12 and each extending from the exterior of the tip, through the tip, and terminating in the sensing membrane when the probe is not in use. The thrust nozzle 12 is in communication with the axial bore 8 of the piston.

The piston 5 further comprises a counterbalancing weight 16 at its rear end 6 for counterbalancing the weight of the disposable tip 11. The counterbalancing weight comprises a stopping surface 20 for engaging with the front bearing adaptor 3 when the piston is in a fully extended state, in order to prevent the piston from sliding out of the housing.

The probe includes an inlet tube 17 for admitting air to the pressure chamber 10, and an outlet tube 18 for connection to a pressure sensing device (not shown) which is incorporated in a computerised tonograph.

The main body 2 further comprises an integral wire guide 19 through which power supply electrical wires are connected to the LED 9. An end plug 21 is fitted in the rear end of the main body 2 of the housing 1 and comprises an integral optical fibre guide 22. In use, an optical fibre may be fed into the fibre optic light guide 22 in the plug 21 at the rear of the probe and may be connected to, or be in optical communication with, the LED in order to carry light from the LED to the exterior surroundings of the probe so that the probe operator may check that the LED is functioning properly throughout the time taken to perform intra-ocular pressure measurements on the patient's eye.

The diameter of the restricting axial bore 8 of the piston 5 is sufficiently small to maintain a pressure differential between the pressure chamber and the tip 11 which remains substantially constant while air flows through the probe (exiting the tip 11 through the exhaust ports 15), the magnitude of this pressure differential being independent of the chamber pressure. The cross-sectional area of the rear face 23 of the piston is sufficiently large that the pressure differential resiliently biases the piston forwards until the stopping surface 20 of the counterbalancing weight 16 comes into contact with the front bearing adaptor 3. This effect is achieved by a piston having an axial bore diameter of about 1.0 mm or less and a rear face having an area of 2.5 mm$^2$ or more. In the embodiment of FIG. 1 the diameter of the restricting axial bore is 0.7 mm. In use these dimensions produce a pressure differential of approximately 0.1 mm Hg.

The front bearing adaptor is made of Torlon (Registered Trade Mark), a polyamide-imide with graphite and fluorocarbon, which exerts sufficiently low friction on the piston to enable the piston to move substantially freely in the bearing 4 in response to movements of the eye, or changes in the intra-ocular pressure. The piston 5 is made of an aluminium alloy, in order to minimise inertia of the piston and is between 25 and 30 ml long. In the embodiment of FIG. 1, the piston is 27 mm long.

Torlon material is known to exhibit sufficiently high tolerance to temperature changes to prevent substantial inaccuracies in measurements obtained using the probe when the probe is operated in varied temperature surroundings.

The disposable tip 11 and the main body 2 are also made of materials chosen for their relatively light weights and high temperature tolerances. The tip is injection moulded in a medical grade clear polycarbonate known as Lexan (Registered Trade Mark). Additionally, the piston dimensions are sufficiently small to avoid creating undesirably large forces on the piston due to pressure in the chamber, which forces would tend to disturb the eye physiology and increase the intra-ocular pressure.

The counterbalancing weight 16 on the rear end 6 of the piston also acts to reduce friction between the piston and the air-tight bearing 4.

The lighter materials and lower frictional effects have the advantage of enabling substantially similar intra-ocular pressure measurements to be achieved with the patient in either a generally a horizontal or a generally vertical position.

The membrane 13 is made of a polyurethane material of medical grade and is approximately 25 thick, having a minimum impact on the air flow in the thrust nozzle and the measured eye pressure.

In operation, the inlet tube 17 is connected to a regulated air supply (not shown) and compressed air flows through the tube 17 into the pressure chamber 10. The air then flows along the restricting axial bore 8 of the piston 5 and through the thrust nozzle 12 until it hits the membrane 13 which, in turn, pushes the membrane away from the thrust nozzle 12 and allows air to escape from the tip 11 through the exhaust ports 15.

When the membrane 13 is placed onto the surface of the cornea of the patient's eye the gap between the membrane 13 and the thrust nozzle 12 is reduced. This restricts air leaving the tip through the exhaust ports 15 (although an air flow through the probe is maintained) and causes a build up of pressure in the pressure chamber. This increase in pressure is monitored down the outlet tube 18 by the pressure sensing device of the tonograph.

In this embodiment, during monitoring of intra-ocular pressure changes the membrane of the sensing tip is applied to the eye and the operator of the probe pushes the housing towards the eye so that piston 5 is forced back into the housing by the patient's eye until it is extended to only substantially halfway towards its fully extended position. The force applied by the operator to applanate the cornea is chosen such that the cornea will never be applanated or flattened over a greater area than the area of the sensing membrane 13. The membrane 13 is subject to the pressure in the thrust nozzle on one side and the eye pressure on the other side. At equilibrium, the pressure is the same on each side and the membrane is substantially flat on the cornea. The pressure in the chamber 10 acting on the piston holds the piston in contact with the eye by a force that is related to the intra-ocular pressure. Contact with the cornea is maintained if the eye moves during testing, especially if the eye moves away from the sensing membrane, due to the pressure differential across the length of the piston 5 acting to resiliently bias the piston forwards.

In this embodiment the maximum available air pressure in the chamber 10 is set at approximately 500 m Hg. The actual pressure in the chamber, determined by the intra-ocular pressure of the patient's eye, is generally in the region of 10 to 20 mm Hg, dependent upon the patient. (The pressure drop across the bearing 4 is negligible, being approximately 20 mm Hg at the maximum chamber pressure of 500 mm Hg.) During testing the flow of air through the probe is approximately 380 ml per minute.

The pressure in the chamber 10 is continuously monitored while the membrane is in contact with the patient's eye by the pressure sensing means connected to the outlet tube 18 and incorporated in the computerised tonograph. This is achieved by making approximately two hundred measurements of pressure per second. The tonograph processes these measurements to produce a digital description of the dynamic intra-ocular pressure waveform. This waveform may then be analysed to determine the pulsatile ocular blood flow.

During use the LED is operated in its light emitting state and the patient focuses the eye along the axial bore 8 of the piston 5 in order to view the source of the emitted light. In this manner the patient readily aligns the eye such that the piston is substantially perpendicular to the applanated cornea and the membrane 13 is substantially parallel to the cornea, this being the arrangement which is known to produce the most accurate measurement of intra-ocular pressure.

The LED arrangement for improving patient alignment with the probe, together with the favourable weights, dimensions and materials of the described component parts of the probe of the present invention, enable intra-ocular pressure measurements of high accuracy and repeatability to be obtained without undesirably large forces being exerted upon the eye. By graphically recording the measurements of continuous intra-ocular pressure obtained using the probe on a patient's eye, for example in the computerised tonograph, this in turn enables the pulsatile ocular blood flow to be calculated with a high degree of accuracy and consistency.

We claim:

1. A pneumatic pressure probe operable with a source of pressurized air and air pressure sensor comprising a housing defining therewithin a pressure chamber having an inlet port connectable to the pressurized air source and an outlet port connectable to the air pressure sensor;

a piston having an axial bore which is in communication with said pressure chamber and through which fluid flows, a proximal end of said piston being received in said pressure chamber and a distal end of said piston extending out from said housing;

a sensing head associated with said distal end of said piston and comprising a transparent sensing membrane, an interior channel which is in communication with said axial bore of said piston and having at least one air outlet port for air flowing through said probe to exit;

said piston being responsive to a pressure differential between said distal and proximal ends of said piston created by air flow through said probe to resiliently bias said piston towards a fully extended position; and light emitting means mounted in said housing, said light emitting means in use emitting light which is visible through said transparent sensing membrane.

2. A pneumatic pressure probe according to claim 1 in which said sensing head is mounted on said distal end of said piston.

3. A pneumatic pressure probe according to claim 2 in which said axial bore of said piston is of a diameter sufficiently small to maintain said pressure differential substantially constant.

4. A pneumatic pressure probe according to claim 2 in which said proximal end of said piston has an end surface on which said air in said pressure chamber acts to urge said piston towards said fully extended position.

5. A pneumatic pressure probe according to claim 2, in which said sensing head is a disposable sensing head comprising an integral transparent membrane.

6. A pneumatic pressure probe according to claim 1, further comprising weighting means located on said piston for counterbalancing the weight of said sensing head.

7. A pneumatic pressure probe according to claim 1, further comprising a substantially air-tight bearing in which a portion of said piston is slidably received.

8. A pneumatic pressure probe according to claim 7, in which said bearing is made of a graphite polymer composite.

9. A pneumatic pressure probe according to claim 7 in which said housing comprises a main body and a replaceable front member comprising said air-tight bearing.

10. A pneumatic pressure probe according to claim 1 in which said piston is made of an aluminum alloy.

11. A pneumatic pressure probe according to claim 1 in which the length of said piston is between substantially 25 and 30 millimeters.

12. A pneumatic pressure probe according to claim 1 in which said light emitting means is a low voltage light emitting diode.

13. A pneumatic pressure probe operable with a source of pressurized air and an air pressure sensor comprising a housing defining therewithin a pressure chamber having an inlet port connectable to the pressurized air source and an outlet source connectable to the air pressure sensor;

a piston having an axial bore which is in communication with said pressure chamber and through which air flows, a proximal end of said piston being received in said pressure chamber and a distal end of said piston extending out from said housing;

a sensing head associated with said distal end of said piston and comprising a transparent sensing membrane, an interior channel which is in communication with said axial bore of said piston and having at least one air outlet port for air flowing through said probe to exit;

said proximal end of said piston having an end surface responsive to a pressure differential between said distal and said proximal ends of said piston created by air flowing through said probe to resiliently bias so as to urge said piston towards a fully extended position;

said axial bore of the piston being of a diameter sufficiently small to maintain said pressure differential substantially constant; and light emitting means mounted in the housing, said light emitting means in use emitting light which is visible through said transparent sensing membrane.

14. A pneumatic pressure probe operable with a source of pressurized air and an air pressure sensor comprising a housing defining therewithin a pressure chamber having an inlet port connectable to an air source and an outlet port connectable to a sensor;

a piston having an axial bore which is in communication with said pressure chamber and through which air flows, a proximal end of said piston being received in said pressure chamber and a distal end of said piston extending out from said housing;

a sensing head associated with said distal end of said piston and comprising a transparent sensing membrane, an interior channel which is in communication with said axial bore of said piston and having at least one outlet port for air flowing through said probe to exit;

light emitting means mounted in said housing, said light emitting means in use emitting light which is variable through said transparent sensing membrane; and means for resiliently biasing said piston towards a fully extended start position such that when said probe is in use said piston is forced back into said housing against said resilient biasing.

\* \* \* \* \*